US006466318B1

(12) United States Patent
Agrawal et al.

(10) Patent No.: US 6,466,318 B1
(45) Date of Patent: Oct. 15, 2002

(54) DEVICE FOR MEASURING PARTICULATE VOLUME AND MEAN SIZE IN WATER

(75) Inventors: Yogesh C. Agrawal, Mercer Island, WA (US); Henry Charles Pottsmith, Seattle, WA (US)

(73) Assignee: Sequoia Scientific, Inc., Redmond, WA (US)

(*) Notice: Subject to any disclaimer, the term of this patent is extended or adjusted under 35 U.S.C. 154(b) by 0 days.

(21) Appl. No.: 09/710,424

(22) Filed: Nov. 8, 2000

Related U.S. Application Data

(63) Continuation-in-part of application No. PCT/US99/10015, filed on May 7, 1999.
(60) Provisional application No. 60/084,770, filed on May 8, 1998.

(51) Int. Cl.[7] .............................................. G01N 15/02
(52) U.S. Cl. ..................... 356/336; 356/340; 356/343
(58) Field of Search ................................. 356/335, 336, 356/337, 338, 339, 340, 341, 342, 343

(56) References Cited

U.S. PATENT DOCUMENTS

| | | | |
|---|---|---|---|
| 3,809,478 A | * | 5/1974 | Talbot |
| 3,835,315 A | * | 9/1974 | Gravitt, Jr. |
| 3,873,206 A | * | 3/1975 | Wilcock |
| 4,037,964 A | * | 7/1977 | Wertheimer et al. |
| 4,037,965 A | * | 7/1977 | Weiss |
| 4,052,600 A | * | 10/1977 | Wertheimer |
| 4,167,335 A | * | 9/1979 | Williams .................... 356/336 |
| 4,882,478 A | * | 11/1989 | Hayashi et al. ............. 356/343 |
| 5,104,221 A | * | 4/1992 | Bott et al. ................... 356/336 |
| 5,416,580 A | * | 5/1995 | Trainer ........................ 356/336 |
| 5,936,729 A | * | 8/1999 | Igushi ......................... 356/336 |

* cited by examiner

Primary Examiner—Hoa Q. Pham
(74) Attorney, Agent, or Firm—Graybeal Jackson Haley LLP

(57) ABSTRACT

The invention is a submersible laser scattering instrument that measures particle total volume, particle total area and Sauter mean diameter. It allows a single calibration for all particle sizes 1.2–250 $\mu$m. A beam of laser light is directed across a void where a sample of water containing particles is admitted. After passing through the water, the light which is forward scattered out of the direct beam falls on two detectors at the same time. The first detector has an active surface shape which is configured to produce an output signal proportional to total particle area at varying total particle areas. The second detector has an active surface shape which is configured to produce an output signal proportional total particle volume varying total particle volumes. Each detector falls within in a radius surrounding the unscattered beam of light. At each annulus within this circle, whether the annulus is described as having a finite width or an infinitely small width, the active surface shape of each detector intercepts less than the entire annulus. The active surface shape of the detector for area increases with distance from the axis of the beam at an increasing rate. The active surface shape of the detector for volume decreases with distance from the axis of the beam at a decreasing rate. The two measured outputs are then electronically combined to obtain mean diameter for the measured particles.

18 Claims, 1 Drawing Sheet

DEVICE FOR MEASURING PARTICULATE VOLUME AND MEAN SIZE IN WATER

This is a continuation-in-part of PCT/US99/10015, filed on May 7, 1999, which claims priority from provisional application No. 60/084,770, filed on May 8, 1998.

FIELD OF INVENTION

The invention is a submersible laser scattering instrument that measures particle total volume, particle total area and Sauter mean diameter. It allows a single calibration for all particle sizes 1.2–250 $\mu$m.

BACKGROUND

Prior Sensors for Sediments: In most cases, suspended sediment 'concentration' has been estimated via one parameter—optical transmission, optical backscatter, or acoustic scattering cross-section. A one-parameter sensor necessarily obtains a weighted sum of the concentrations of underlying size classes. For example, optical transmission or backscatter sensors estimate approximate (not exact) total particle area. In contrast, acoustic sensors, usually operating in the Rayleigh regime [i.e,. when the insonifying acoustic wavelength $\lambda_a$ is of the same order or greater than the particle diameter, i.e. $k_a a < 1$ where $k_a = 2\pi/\lambda_a$] respond to the sum of the squares of particle volumes. This condition is satisfied for particles of 1 mm diameter or smaller at acoustic frequencies of 1 MHz or lower. Neither of these sensors simply sum the mass or volume concentrations to provide the needed measure of $C_n$ or the total concentration $C_n$. For this reason, unless the particle size distribution is invariant in space and time, the calibration of these single-parameter sensors in laboratories before field usage, while a common practice, is of limited value. The most unfortunate consequence of the use of such calibrations is the lack of even the error bounds in the interpretation of data. Certainly, historical data with these unknown errors are in part responsible for the large variability in predictive capability of sediment transport models.

Optics affords a capability to observe a wide range of particle sizes. By measuring optical scattering over a wide dynamic range of angles [dynamic range is defined here as the ratio of maximum to minimum scattering angle], a measurement is obtained with information content on a correspondingly large dynamic range in particle sizes. The angular dynamic range is typically 100:1 or 200:1 so that size ranges from, say, 1–200 microns can be studied with a single instrument. This principle is called laser diffraction. The name derives from the approximation to the exact solution to Maxwell's equations describing light scattering by spheres. The exact solution for homogeneous spheres of arbitrary size, due to [Mie, 1908], has the property that for large particles, i.e. when the real part m of the complex refractive index, and particle size ka (k being $2\pi/\lambda$, $\lambda$ is optical wavelength) are such that $(m-1)ka \gg 1$, the scattering at small forward angles appears nearly identical to the diffraction through an equal diameter aperture (see [Bom and Wolf, 1975]). An even more significant observation is that under these conditions, the refractive index of particles becomes largely irrelevant. This implies that the particle composition, or for that matter, possibly particle internal structure and homogeneity, are of little to no consequence. As the particle composition does not determine its scattering characteristics, the method is fully general for particle sizing. It is for this reason, that this has become the most widely used particle sizing method, employed for measuring diverse types of particles, including cements, chocolates or microbes.

The first underwater instrument based on laser diffraction was developed by [Bale and Morris, 1987]. They adapted a commercial laboratory instrument manufactured by Malvern Instruments of UK for ocean use. They have presented results from estuarine particle sizing [Eisma, 1996]. Recently, a team of French scientists has employed a submersible instrument manufactured by CILAS ([Petrenko et al., 1997], [Gentien et al., 1995], [Lunven et al., ]). Multi-angle scattering was observed using a CCD line array photo-detector ([Agrawal and Pottsmith, 1994]). The use of CCD's unnecessarily required long averaging times to remove the influence of laser speckle, and also required complex, fast electronics.

SUMMARY OF THE INVENTION

The invention is referred to as the LISST-25. Based on laser diffraction technology, the LISST-25 is designed to record the total suspended particle area and volume concentrations, and the Sauter mean diameter of suspended particles. The main advantage of the LISST-25 is that, unlike transmissometers, optical backscatter sensors, or single-frequency acoustic sensors, the LISST-25 has a constant calibration over the covered range of particle sizes. The LISST-25 does not give the particle size distribution.

The technique used by the LISST-25 sensor differs from other turbidity sensors. It measures the forward scattered light from a collimated laser beam using only two specially designed silicon detectors. These measurements are used to obtain the total volume and total area of particles directly, bypassing inversion of data as is done in other instruments to obtain the particle size distribution. From the ratio of total volume and area, the Sauter mean diameter is obtained.

The LISST-25 is a self-contained instrument that includes optics and electronics, datalogger, and a battery pack. The on-board data logger allows for simple programming of sampling schedules and can be connected to a personal computer via an RS-232port. The depth rating is 300 meters. The instrument covers a wide dynamic range of concentrations, from 0.1 to 1,000 mg/l (microliters/liter). The operational limit of the instrument is based on optical transmission of water, i.e., beam c range between 0.5 m$^{-1}$ to 25 m$^{-1}$.

In one aspect, the invention is an instrument based on scattering of laser light for measuring both total particle volume and total particle area at the same time for particles suspended in water. A beam of laser light is directed across a void where a sample of water containing particles is admitted. After passing through the water, the light which is forward scattered out of the direct beam falls on two detectors at the same time. The first detector has an active surface shape which is configured to produce an output signal proportional to total particle area at varying total particle areas. The second detector has an active surface shape which is configured to produce an output signal proportional total particle volume varying total particle volumes.

Each detector falls within in a radius surrounding the unscattered beam of light. At each annulus within this circle, whether the annulus is described as having a finite width or an infinitely small width, the active surface shape of each detector intercepts less than the entire annulus. The active surface shape of the detector for area increases with distance from the axis of the beam at an increasing rate. The active surface shape of the detector for volume decreases with distance from the axis of the beam at a decreasing rate.

In the preferred embodiment, the output from each detector is directly proportional to the quantity to be measured.

This is accomplished by the carefully designed shape of each detector. These two measured outputs are then electronically combined to obtain mean diameter for the measured particles.

In the preferred embodiment, the two detectors are both fabricated on a single semiconductor substrate plate made of silicon. Each detector is formed of conventional photodiode material deposited on the silicon plate. Alternatively, the invention may be embodied in two separate detectors on separate substrates. Whether formed on a single substrate or two substrates, instead of depositing the photodiode material on the substrate in the desired active surface shape, the preferred active surface shape may be achieved by placing a mask on top of photodiode material with an active surface area larger than the desired active surface shape. The mask can simply cover the periphery beyond the desired shape or it can be comprised of a pattern of dots or checkerboard or other shapes of alternating opaque and transparent portions. The opaque and transparent portions are configured such that only the desired portion of each annulus at a distance from the axis of the beam of light passes light to the active surface of the photodetector.

In a second aspect, the invention is an instrument which includes only a single detector, either one of the detectors described above.

DETAILED DESCRIPTION

Figure 1:
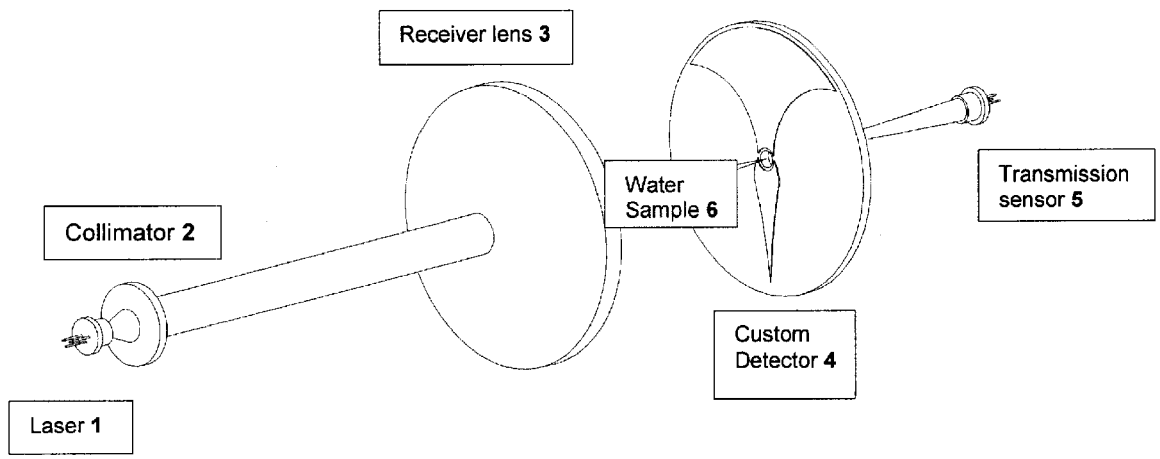
FIG. 1 shows the important optical components.

The signature of particle size is described in simple physical terms. Consider the scattering of collimated laser light by small particles as detected by a specially constructed detector as shown in FIG. 1. The detector is placed at the focal plane of a receiving lens of focal length f. As a result, all rays originating from a scatterer at a particular angle to the lens'optical axis reach a point on the focal plane at a radius $r=f\theta$.

The main laser beam passes through a hole in the center of the detector and is detected by a photo-diode placed behind the detector. This provides the optical transmissometer function.

The scattered intensity due to larger particles peaks at small angles, and vice versa. Since the scattering is linear, the total optical power distribution sensed by the detector is simply the sum of the contributions from each size class, weighted by the concentration in that size class.

Figure 2:
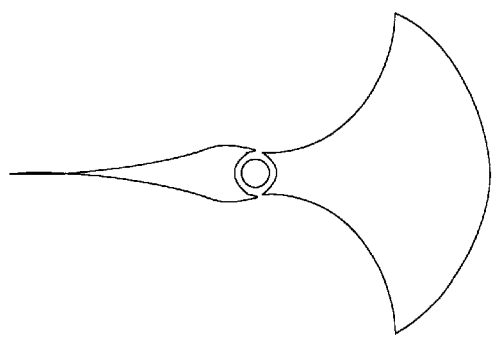
FIG. 2 shows the preferred form of the detector.

The range of sizes of particles that can be observed by this system is established as follows. The largest observable particles are those that put the peak of their scattering at the inner-most portions of the detector. Similarly, the smallest observable particles are those that put their energy maximum at the periphery. Since the rings of FIG. 2 are logarithmic in radii, thus arranged for mathematical reasons, and since it is obvious that the size classes be chosen so that each size class corresponds to a matching ring, it follows that the size classes are also separated in a logarithmic order. Furthermore, as each ring itself observes scattering over a small subrange of angles, it follows that each ring also observes a subrange of particle sizes.

The inner radius of a ring corresponds to the largest particles, whereas the outer radius of the ring corresponds to the smallest particles in the corresponding size subrange, or size class. The relationship between particle size a and the corresponding center of scattered light intensity on the detector $\theta_c$ is related to the optical wave vector k, as:

$$ka\theta_c = \beta_{opt}$$

We set the constant $\beta_{opt}$ to be 2. For example, given a minimum angle at which scattering is observed to be 0.85 mrad, the largest diameter of particles that can be observed with a 0.67 nm wavelength laser is 500 microns.

The total volume concentration in the sample can be obtained by summing this volume distribution. In this manner, the true particle concentration of particles $C_n$ is obtained, regardless of particle density or size distribution. It also follows that since a total is measured, the calibration of the measurement of total suspended volume of particles is not affected by a change in size distribution of the particles. The instruments can be tested to this standard in the laboratory, where sphericity and homogeneity of particle composition is easily assured. A crucial test of this idea is to examine experimentally, if the relationship between actual known volume concentration and reported concentration falls on a common single straight line for different particles and suspensions.

Now, the ratio of the total particle volume to the total particle area is defined as Sauter Mean Diameter, SMD. Thus, the data permit an estimation of SMD.

We have deliberately insisted on the use of the term 'volume concentration' in this work as the quantity measured by laser diffraction instruments. This is to emphasize that the method does not obtain any information about particle mass density.

It is noted that whereas the calibration of laser diffraction methods is largely insensitive to particle composition, minor errors can be expected to arise depending on particle refractive index. The errors become significant when the refractive index of particles used in the computation of the scattering matrix is vastly different from the particles being analyzed. The use of the correct forward matrix can obviate this difficulty, though in nature, this is not always an option.

In FIG. 1, we show the optical schematic. A 10 mW diode laser 1 is used as the light source. This 670 nm laser is coupled to a single-mode (SM) optical fiber (not shown). SM fiber is used because it preserves the wave-front purity of the exiting light and also because SM fibers enable the tightest beam collimation. The SM fibers are angle-polished at the entrance and exit, in order to suppress back-reflection that cause instability of the laser. At the SM fiber exit, a pure, single transverse mode beam emerges. This is coupled to an achromatic collimating lens 2. Achromats are used because they are also corrected for spherical aberration.

The laser optical path exits a small window into water. The beam diameter in water is 6 mm and the optical path in water is 5 cm. Longer or shorter path may be dictated by the range of optical conditions to be encountered. The laser beam illuminates particles in water and then reenters the pressure housing through a larger window. These two windows, being in the optical train, are polished to a very high degree and the air-sides are anti-reflection coated. The direct beam now focuses to a waist at the focal plane where the detector is placed. The inner radius of the detector is 102 microns and the outer radius is 20 mm. At the center of the detector exists a laser-drilled hole to pass the direct beam through the silicon. The transmitted beam power is sensed with a silicon photo-diode placed behind the detector. This photo-diode constitutes the optical transmissometer function. The overall sensitivity of the detectors is 2.44 nA per digital count. With a typical silicon responsivity of 0.4 A/W, this implies an optical power resolution of nearly 6 nW. The amplifiers have a 3 dB low-pass cut off at 10 Hz. The low bandwidth is employed to minimize shot-noise of optical detection [Yariv, 1985 #1170]. Electronic amplification noise is less than one count The fastest rate at which scattering data can be acquired is 5 Hz, limited only by the low-power data-acquisition computer.

The amplified outputs of the detectors are stored in memory on board the computer controlling each instrument. The on-board computer is programmable to take scattering data samples at any arbitrary schedule, but not at a higher than 5 Hz rate. For all cases, a background scattering distribution is measured and stored. The source of this scattering is micro-roughness on optics. This background is termed zscat.

The measured data from particles is attenuated by the factor $\tau = \exp(-cl)$ in accordance with Beer's law, where c is the beam attenuation per meter and l is the optical pathlength, l=5 cm. The attenuation is estimated from the ratio $\tau = T/T_o$, where T is transmitted power, normalized by its value $T_o$ when the background measurement is made using highly filtered pure water. The corrected scattering from a sample of water is then obtained as:

$$s = [d/\tau - zscat$$

where d is the scattering distribution as recorded from a sample containing particles under measurement, and the quantities s, d and zsc are in digital counts. The vector s is then corrected for non-ideal detector responsivity correction factor D (see below) to produce a fully corrected scattering data S, still in digital counts:

$$S(i) = s(i)D(i)$$

An unfortunate consequence of the relatively small sample-volume dimensions of the laser diffraction instrument (typical volume is 2 cm³) is that when the number density of particles is small, as is typical for the largest particles (e.g. marine aggregates), statistical variability of the particle number in the sample volume itself becomes large. In interpreting field data, it is important to bear this in mind. Of course, averaging over several scans, in effect, increases the sample volume size and thereby reduces this variability.

Optical Attenuation

Let the laser output power be $P_l$. If $\eta_{opt1}$ is the overall optical efficiency of the components till the laser beam enters water, then the laser power entering water will be = $\eta_{opt1} P_l$. For the sake of simplicity, let $P_o = \eta_{opt1} P_l$. Consider first the case of pure filtered water. The power reaching the receiving window will be attenuated due to absorption in water. It is conventional in ocean optics literature to use the symbol a for pure water absorption (in m$^{-1}$) so that the laser power reaching the receiving window will be $e^{-al} P_o$. Further optical losses due to reflections off optical surfaces can be included as another optical efficiency factor, $\eta_{opt2}$ so that the power sensed by the 'transmissometer' photodiode is $e^{-al} P_o \eta_{opt2}$. Combining the factors $\eta_{opt1} \eta_{opt2}$ into an overall optical efficiency $\eta_{opt} = \eta_{opt1} \eta_{opt2}$, one sees that for the case of pure water, the 'transmissometer' diode sees a laser power given by $$P_{t,clear} = e^{-al} \eta_{opt} P_l \quad (A1)$$

The introduction of absorptive and/or scattering material, with an additional attenuation of light by absorption and scattering represented by $c_A (m^{-1})$, will clearly change the power incident on the transmissometer photodiode to $$P_{t,turbid} = \exp\{-(a + c_A) l\} \eta_{opt} P_l \quad (A2)$$

From the ratio of A2 and A1, the transmissometer photodiode measures the additional $c_A$ due to the dissolved and suspended material. When there is no dissolved absorbing material and the particles are non-absorbing, $c_A = b$, the total scattering, so that a direct measure of total scattering by particles is obtainable. In general, the measured attenuation will be the sum of that due to absorption and scattering by particles and due to dissolved absorptive material. Water absorption is not accessible.

Background Light

The measurement of background light and its adequate subtraction from the total signal at the detector is important, especially when the scattering from particles is comparable in magnitude. If the background light is measured in the absence of scattering particles, then this background field should be first attenuated by $\exp(-c_A l)$ before subtracting from the measurement which is the combined signal from particles and optical surfaces.

Shape of the Dectectors

A diode laser is collimated using standard optics. The collimated beam illuminates particles in water. Light scattered by particles enters an enclosure wherein it is gathered by a receiving lens. In the focal plane of the receiving lens, any point at a distance r away from the center corresponds to a unique scattering angle $\theta = r/f$. Thus measurements of the scattered optical power at a number of radii $r_i$, defines an observation array E. The array E can be described in terms of the scattering properties of particles and the number density, N, of particles;

FIG. 1 shows the basic optics of the LISST-25 instrument with a laser 1, collimating lens 2, receiving lens 3, the detector plane where the custom detector is placed 4, and the transmission sensor 5.

$$E = KN \quad (i)$$

where K is a 2-dimensional matrix, each element of which represents the scattered power at a particular angle, from a single particle of a single size.

For clarity, a few definitions are offered:

n(a) Number density of particles of radius a, so that the number of particles per unit volume of water, between the size a and a+ a is n(a) a. The symbol N is a discreet form of n(a); i.e. there are, say 32 size classes that make up a 32-element array N.

n(a) a² Area density of particles of radius a, so that the area of particles per unit volume of water, between the size a and a+ a is a²n(a) a. The symbol $N_A$ is a discreet form of n(a) a²; i.e. there are, again, 32 size classes that make up the 32-element array $N_A$.

4/3 πn(a)a³ Volume density of particles of radius a, so that the volume of particles per unit volume of water, between the size a and a+ a is a³n(a) a. The symbol $N_V$ is a discreet form of n(a)a³; i.e. there are, again, 32 size classes that make up the 32-element array $N_V$.

The Total Area Concentration of particles is the sum of all the 32 elements of $N_A$. Similarly, the Total Volume Concentration of particles is the sum of all the elements of $N_V$.

The LISST-25 obtains the total volume concentration and total area concentration by weighted sum of the elements of the observation array E. Thus two sets of weight functions $W_A$ and $W_V$ are defined in a manner so that;

Total Area Concentration=$\Sigma_i E_i W_{Ai}$; $E_i$ is an element of E, $W_{Ai}$ is an element of $W_A$; (ii)

Total Volume Concentration=$\Sigma_i E_i W_{Vi}$; $W_{Vi}$ is an element of $W_V$ (iii)

The computations of the weight functions $W_A$ and $W_V$ is done in a manner indicated below. Once the weight functions $W_A$ and $W_V$ have been computed, they become fixed constants applicable in the manner of equations (ii) and (iii).

The application of the weight functions to the spatial structure of the light intensity in the focal plane of the receiving lens produces a specially shaped detector. This detector is shown in FIG. 2. This is a frontal view of the detector that is shown edge-on in FIG. 1.

The small-angle scattering of laser light by particles (i.e. the intensity variation seen away from the axis of the optics in our FIG. 1 has the convenient property that its magnitude and angular dependence is relatively insensitive to particle composition. For this reason, the method is quite generally applicable to all types of particles, and it is widely used in laboratories and industry. It is commonly known as Laser Diffraction (from the small angle scattering by a particle looking like diffraction through an aperture).

The angular scattering in the focal plane of a lens can be expressed as:

$$\underline{E}_A = K_A N_A \quad \text{(i)}$$

where:

$E_A$: Scattered power sensed at an angle from the optical axis;

$K_A$: Kernel matrix, denoting scattering vs. angle per unit particle area $N_A$: Area Distribution, $a^2 n(a)$. $N_A$ is a, say, 32-element array; each element area representing a range of sizes; and the full array representing a typical 200:1 size range.

Similarly, for scattered power per unit volume:

$$\underline{E}_V = K_V N_V \quad \text{(ii)}$$

where:

$E_V$: Scattered power sensed at an angle from the optical axis $K_V$: Kernel matrix, denoting scattering vs. angle per unit particle volume $N_V$: Area Distribution, $a^3 n(a)$. $N_V$ is a, say, 32-element array, as above.

One then seeks a pair of filter vectors $\underline{T}_A$ and $\underline{T}_V$ (each containing 32 elements in the example used here) such that when the scalar product with the unit vector U is carried out:

$$\underline{T}_V \underline{E}_V = U N_V \text{ or } = \Sigma_i N_{Vi} \text{ i.e. Total volume} \quad \text{(iii)}$$

and $$\underline{T}_A \underline{E}_A = U N_A \text{ or } = \Sigma_i N_{Ai} \text{ i.e. Total Area} \quad \text{(iv)}$$

and $$\text{Sauter Mean Diameter } (SMD) = 3/2 T_V/T_A \quad \text{(v)}$$

Thus, solving for equations (iii) and (iv) requires solving:

$$\underline{T}_V \underline{K}_V = U \quad \text{(vi)}$$

and $$\underline{T}_A \underline{K}_A = U \quad \text{(vii)}$$

The solution involves computation of equations (vi) and (vii) with a positivity and smoothing constraint; i.e. the filter coefficients (also called weight factors or weight functions) $\underline{T}_V$ and $\underline{T}_A$ are positive and also vary smoothly.

The annular extent of each detector is made proportional to the weight factors (filter coefficients) $T_V$ and $T_A$. For example, if $T_V$ were constant, then the detector would have a constant annular extent, and it would be wedge shaped. If $T_V$ varies over a range 1000:1, and if the detector is a semicircle (180 degrees) at the smallest radius (see the comet-shaped detector) then, the tail of the comet will cover only 180/1000 or 0.18 degree.

The magnitude of $T_V$ does, in fact, vary from near one-thousand near the optical axis, to about 1 at the edge of the detector. This is why the detector becomes thinner away from the optical axis. In contrast, $T_A$ is mostly of magnitude unity, varying to within a factor 2 at both extremes (from lens axis to outside edge of detector). This is why the area sensing detector is most like a wedge.

The detector consists of two pieces of photosensitive silicon on a substrate. In the center of the substrate is a hole for the passage of the focused direct laser beam. The power of the transmitted beam is sensed by a separate photodiode. This is an auxiliary measurement. It is used to apply correction in estimates of total area and volume concentrations due to attenuation of the beam.

FIG. 2 shows the custom detector that is at the heart of the LISST-25. This is a frontal view of the detector shown edge-on in FIG. 1. The shaded wedge shape on the left measures the total area concentration; the comet shaped detector on the right measures the total volume concentration. The hole in the center passes the laser beam for measurement of optical transmission.

Three photodetector signals are sensed corresponding, respectively, to total area concentration, total volume concentration, and the optical transmission. Each photocurrent is sensed using a standard transimpedance amplifier.

BIBLIOGRAPHY

Agrawal, Y. C., and H. C. Pottsmith, Laser diffraction particle sizing in STRESS, *Cont. Shelf Res.,* 14 (10/11), 1,101–1,121, 1994.

Bale, A. J., and A. W. Morris, In Situ measurement of particle size in estuarine waters, *Estuarine, Coastal and Shelf Science,* 24, 253–263, 1987.

Born, M., and E. Wolf, *Principles of Optics,* Pergamon Press, 1975.

Eisma, D., Bale, A. J., Dearnaley, M. P., Fennessy, M. J., W. Van Leussen, Maldiney, M. A. Pfeiffer, A. and J. T. Wells, Intercomparison of in-situ suspended matter (floc) size measurements, *Journal of Sea Research,* 36 ((1/2)), 3–14, 1996.

Lunven, M., P. Gentien, and P. Doillet, Suspended sediments in a Macrotidal Estuary: Comparison and use of different sensors biases,, 1–10 also includes FIGS. 1–14.

Mie, G., Contributions to the optics of suspended media, specifically colloidal metal suspensions, *Ann. der Physik,* 25, 377–455, 1908.

Petrenko, A. A., B. H. Jones, T. D. Dickey, M. LeHaitre, and C. Moore, Effects of sewage plume on the biology, optical characteristics, and particle size distribution of coastal waters, *Journal of Geophysical Research,* 102 (C11), 25,061–25,071, 1997.

We claim:

1. A light scattering instrument for measuring total particle volume and total particle area at the same time for particles suspended in water, comprising:

a. a sample void where water containing particles is admitted;

b. beside the sample void, a source of a beam of light directed at the sample void; and c. on an opposite side of the sample void, i. a first light power detector with an active surface shape configured to receive forward scattered light and produce an output signal which is proportional to total particle area at varying total particle areas, the active surface shape of the first light power detector intercepting less than an entire annulus at each distance from an axis of the beam, the portion of an annulus intercepted increasing at an increasing rate with distance from the axis of the beam; and ii. a second light power detector with an active surface shape configured to receive forward scattered light and produce an output signal which is proportional to total particle volume at varying total particle volumes, the active surface shape of the second light power detector intercepting less than an entire annulus at each distance from an axis of the beam, the portion of an annulus intercepted decreasing with distance from the axis of the beam.

2. The instrument of claim 1 wherein the portion of an annulus intercepted by the active surface shape of the second detector, for volume, decreases with distance from the axis of the beam at a decreasing rate.

3. The instrument of claim 1 adapted to compute mean particle diameter, further including:

an electronic combining circuit which receives the two output signals and combines the output signals to obtain mean diameter of the particles.

4. The instrument of claim 1 wherein the first light power detector and the second light power detector coexist on a single semiconductor substrate plate.

5. The instrument of claim 1 wherein the first light power detector and the second light power detector each consist of photodiode material with an active surface area larger than the active surface shape for the detector and the photodiode material is covered with a mask which exposes to incident light only the active surface shape for the detector.

6. A method for measuring total particle volume and total particle area at the same time for particles suspended in water, comprising:

a. generating a beam of light;
b. passing the beam of light through water containing particles; and
c. receiving forward scattered light on a first light power detector and a second light power detector,
   i. the first detector having an active surface shape configured to receive forward scattered light and produce an output signal which is proportional to total particle area at varying total particle areas, the active surface shape of the first light power detector intercepting less than an entire annulus at each distance from an axis of the beam, the portion of an annulus intercepted increasing at an increasing rate with distance from the axis of the beam; and
   ii. the second detector having an active surface shape configured to receive forward scattered light and produce an output signal which is proportional to total particle volume at varying total particle volumes, the active surface shape of the second light power detector intercepting less than an entire annulus at each distance from an axis of the beam, the portion of an annulus intercepted decreasing with distance from the axis of the beam.

7. The method of claim 6, wherein the portion of an annulus intercepted by the active surface shape of the second detector, for volume, decreases with distance from the beam at a decreasing rate.

8. The method of claim 6 adapted to compute mean diameter of the particles by further including:

mathematically combining the first and the second output signals to obtain mean diameter of the particles.

9. A light scattering instrument for measuring total area of particles suspended in water, comprising:

a. a sample void where water containing particles is admitted;
b. beside the sample void, a source of a beam of light directed at the sample void; and
c. on an opposite side of the sample void, a light power detector with an active surface shape configured to receive forward scattered light and produce an output signal which is proportional to total particle area at varying total particle areas the active surface shape of the light power detector intercepting less than an entire annulus at each distance from an axis of the beam, the portion of an annulus intercepted increasing at an increasing rate with distance from the axis of the beam.

10. The instrument of claim 9 wherein the light power detector consists of photodiode material deposited on a semiconductor substrate in the shape of the active surface area.

11. The instrument of claim 9 wherein the light power detector consists of photodiode material with an active surface area larger than the active surface shape for the detector and the photodiode material is covered with a mask which exposes to incident light only the active surface shape.

12. A method for measuring total area of particles suspended in water via light scattering, comprising:

a. generating a beam of light;
b. passing the beam of light through water containing particles; and
c. receiving forward scattered light on a light power detector with an active surface shape configured to receive forward scattered light and produce an output signal which is proportional to total particle area at varying total particle areas, the active surface shape of the light power detector intercepting less than an entire annulus at each distance from an axis of the beam, the portion of an annulus intercepted increasing at an increasing rate with distance from the axis of the beam.

13. A light scattering instrument for measuring total volume of particles suspended in water, comprising:

a. a sample void where water containing particles is admitted;
b. beside the sample void, a source of a beam of light directed at the sample void; and
c. on an opposite side of the sample void, a light power detector with an active surface shape configured to receive forward scattered light and produce an output signal which is proportional to total particle volume at varying total particle volumes, the active surface shape of the light power detector intercepting less than an entire annulus at each distance from an axis of the beam, the portion of an annulus intercepted decreasing with distance from the axis of the beam.

14. The instrument of claim 13 wherein the portion of an annulus intercepted by the active surface shape of the detector decreases with distance from the axis of the beam at a decreasing rate.

15. The instrument of claim 13 wherein the light power detector consists of photodiode material deposited on a semiconductor substrate in the shape of the active surface area.

16. The instrument of claim 13 wherein the light power detector consists of photodiode material with an active surface area larger than the active surface shape for the detector and the photodiode material is covered with a mask which exposes to incident light only the active surface shape.

17. A method for measuring total volume of particles suspended in water via light scattering, comprising:
 a. generating a beam of light;
 b. passing the beam of light through water containing particles; and
 c. receiving forward scattered light on a light power detector with an active surface shape configured to produce an output signal which is proportional to total particle volume at varying total particle volumes, the active surface shape of the second light power detector intercepting less than an entire annulus at each distance from an axis of the beam, the portion of an annulus intercepted decreasing with distance from the axis of the beam.

18. The method of claim 17 wherein the portion of an annulus intercepted decreases with distance from the beam at a decreasing rate.

* * * * *